(12) United States Patent
Lemchen

(10) Patent No.: US 8,235,716 B2
(45) Date of Patent: Aug. 7, 2012

(54) METHOD FOR USING RADIO FREQUENCY IDENTIFICATION MICROCHIPS IN ORTHODONTIC BRACKETS

(76) Inventor: Marc Lemchen, New York, NY (US)

( * ) Notice: Subject to any disclaimer, the term of this patent is extended or adjusted under 35 U.S.C. 154(b) by 397 days.

(21) Appl. No.: 12/490,203

(22) Filed: Jun. 23, 2009

(65) Prior Publication Data
US 2009/0317757 A1 Dec. 24, 2009

Related U.S. Application Data

(60) Provisional application No. 61/075,299, filed on Jun. 24, 2008.

(51) Int. Cl.
*A61C 7/14* (2006.01)
(52) U.S. Cl. .............................. 433/24; 705/2
(58) Field of Classification Search .................. 433/8, 9, 433/10, 24; 705/2, 3; 340/10.1, 572.1; 700/115, 700/215; 235/462.46
See application file for complete search history.

(56) References Cited

U.S. PATENT DOCUMENTS

| | | | | |
|---|---|---|---|---|
| 5,464,349 A * | 11/1995 | Andreiko et al. | ............... | 433/24 |
| 6,632,089 B2 * | 10/2003 | Rubbert et al. | ................. | 433/24 |
| 6,688,885 B1 * | 2/2004 | Sachdeva et al. | ............... | 433/24 |
| 6,733,289 B2 * | 5/2004 | Manemann et al. | ............ | 433/24 |
| 2003/0163291 A1 * | 8/2003 | Jordan et al. | ....................... | 703/1 |
| 2003/0224317 A1 * | 12/2003 | Andreiko et al. | ............... | 433/24 |
| 2004/0214128 A1 * | 10/2004 | Sachdeva et al. | ............... | 433/24 |
| 2004/0259049 A1 * | 12/2004 | Kopelman et al. | .............. | 433/24 |
| 2005/0239012 A1 * | 10/2005 | Bathen et al. | ................... | 433/10 |
| 2006/0134580 A1 * | 6/2006 | Raby et al. | ..................... | 433/213 |
| 2006/0172250 A1 * | 8/2006 | Wen | ................. | 433/18 |
| 2010/0152872 A1 * | 6/2010 | Dunne et al. | .................... | 700/98 |

* cited by examiner

*Primary Examiner* — Cris L Rodriguez
*Assistant Examiner* — Justin O'Donnell
(74) *Attorney, Agent, or Firm* — Marcus C. Dawes; Daniel L. Dawes (57) ABSTRACT

The following invention is an apparatus and method for quickly determining the type of bracket implanted on patient's tooth. A radio frequency identification (RFID) microchip is coupled to or in an orthodontic bracket. The bracket or series of brackets are then implanted on the patient's teeth as required. With the RFID in or on the bracket, the orthodontist or staff uses a scanner to read the brackets. The information read by the scanner allows the staff to select the correct corresponding bracket needed for replacement from an inventory. Confirmation of the correct selection is obtained by another scan from another scanner located in the bracket holding device. Not only does this process ensure that the correct replacement bracket is received by the patient, but also provides the orthodontist and staff with a real-time tracking of inventory supply.

19 Claims, 5 Drawing Sheets

METHOD FOR USING RADIO FREQUENCY IDENTIFICATION MICROCHIPS IN ORTHODONTIC BRACKETS

RELATED APPLICATIONS

The present application is related to U.S. Provisional Patent Application Ser. No. 61/075,299, filed on Jun. 24, 2008, which is incorporated herein by reference and to which priority is claimed pursuant to 35 USC 119.

BACKGROUND OF THE INVENTION

1. Field of the Invention

The invention relates to the field of orthodontic brackets, in particular the identification, tracking, and status of the brackets as they are being used in a patient's mouth during orthodontic treatment.

2. Description of the Prior Art

Orthodontic brackets have long been in used in the orthodontic field to assist in the treatment of a variety of cosmetic and structural teeth and jaw problems such as crooked teeth, overbite, and other malocclusions. Typically, an orthodontist assesses the teeth of a patient and determines what prescription of brackets are required for that particular patient's specific needs. Each bracket prescription comprises a plurality of specific pre-selected features such as torque and tip varieties that are machined into the bracket slot. Once fabricated, each bracket is cemented to the patient's teeth with extra attention and consideration given to make sure each bracket is in fact cemented to the tooth for which it was intended. If the bracket becomes broken or if the prescription becomes outdated, a replacement bracket is manufactured, the old bracket is removed, and then the new bracket is inserted into its place.

However, for the entire duration of the patient's orthodontic treatment including the initial selection of the brackets and the replacement of any brackets, the orthodontist must keep track of every detail of patient information on a tooth chart. For example, if a replacement bracket is required, the orthodontist must first refer to the tooth chart for the patient's original prescription for that specific bracket and when the bracket was first installed or fixed on the patient's tooth. The orthodontist then must make sure the proper replacement bracket is acquired and then is in fact applied to the correct tooth. This process is inefficient and time consuming and can lead to mistakes which are preventable.

Also present in the prior art are radio frequency identification (RFID) microchips. The smallest of the RFID chips, also known as "powder" RFID microchips, are typically very small, having a size of just 0.05 mm×0.05 mm and carrying up to 128 bits of ROM for storing a unique 38 digit number. The RFID "powder" chips are small enough to be easily incorporated into thin paper, like that used in paper currency and gift certificates. The RFID chips are also readable from a distance up to 25 cm away with the use of an external antenna that is a fraction of an inch long.

What is needed therefore is an apparatus and method that allows orthodontists and other dental professionals to quickly determine the bracket type present on a patient's tooth and ensure that if any replacement brackets are required, the proper bracket will be installed without error.

BRIEF SUMMARY OF THE INVENTION

The current invention is for a method of using radio frequency identification (RFID) microchips in an orthodontic bracket comprising providing at least one orthodontic bracket with at least one RFID chip coupled to, in or on the bracket, where the RFID chip has recorded thereon information concerning the nature of the bracket, scanning the recorded information from the at least one RFID chip coupled to the at least one bracket, and employing the bracket according to the recorded information scanned from the corresponding RFID chip.

The method above further comprises wherein employing the bracket according to the recorded information scanned out of the corresponding RFID chip comprises using the information for determining an inventory of the brackets.

In another embodiment the method above further comprises wherein employing the bracket according to the recorded information read out of the corresponding RFID chip comprises identifying the bracket type to a user, and where the bracket includes at least one tip machined into a bracket slot and where identifying the bracket type to the user comprises identifying a prescription of the corresponding bracket including but not limited to at least one torque applied to the bracket and/or tip machined into the bracket slot for each corresponding tooth.

In another embodiment the method above further comprises where employing the bracket according to the recorded information scanned out of the corresponding RFID chip comprises identifying a particular targeted bracket in order to produce a patient tooth chart of the bracket location, prescription, including wire slot size, tip structure, torque applied to the bracket, and/or material of manufacture of the bracket.

In yet another embodiment, the method above further comprises replacing the at least one bracket when a change in prescription is needed comprising scanning the outdated bracket being replaced prior to removal, replacing the current patient information with updated scanned information, and documenting in a patient tooth chart correlated to the scanned identification a reason the bracket is being replaced. Alternatively, the method further comprises scanning a replacement bracket to insure that the replacement bracket has a proper prescription.

In yet another embodiment, the method above further comprises where the steps of scanning the recorded information from the at least one RIFD chip coupled to the at least one bracket and employing the bracket according to the information scanned out of the corresponding RFID chip further comprises sending a set of user-entered conditions to a robotic system, the robotic system selecting a bracket based on the set of user-entered conditions, the robotic system scanning the selected bracket, the robotic system confirming that the selected bracket has the set of user-entered conditions, and the robotic system recording that the correct bracket has been selected. Alternatively, the method further comprises the robotic system performing bracket placement into an indirect or direct bonding tray.

In still another embodiment, the method above further comprises where scanning the recorded information from the at least one RFID chip coupled to the at least one bracket comprises scanning the bracket with an RFID scanner disposed within a bracket holding device to scan the recorded information from the RFID chip while the bracket is being held within the bracket holding device, and displaying the recorded information on a display coupled to the bracket holding device to prevent the selection of an incorrect bracket.

In still another embodiment, the method above further comprises where providing at least one orthodontic bracket comprises coupling the RFID chip to the bracket by disposition into a depression on a tooth side base of the bracket, coupling the RFID chip to a recessed hole in a mesh backing of the bracket, or coupling the RFID chip to a lip side of the bracket in a depression or cup and sealing the depression or cup over with a resin sealant.

In another embodiment, the method above further comprises where employing the bracket according to the recorded information scanned from the corresponding RFID comprises using the RFID chip during x-ray and optical dental scans to give scanned information to a software program which uses the scanned recorded information to bend custom wires or plan treatment with specialized orthodontic programs.

The current invention also provides for a method of using radio frequency identification (RFID) microchips in an orthodontic bracket comprising providing a plurality of RFID chips coupled to, on or in a plurality of orthodontic brackets, where the RFID chips have recorded therein information concerning the nature of each corresponding bracket, scanning the recorded information from the plurality RFID chips coupled to the plurality of brackets, and employing the plurality of brackets according to the recorded information scanned out of the corresponding RFID chips. Alternatively, the method further includes wherein employing the plurality of brackets according to the recorded information scanned from the corresponding RFID chips comprises using the information for determining an inventory of the brackets.

In another embodiment, the method above further includes wherein employing the plurality of brackets according to the recorded information read from the corresponding RFID chips comprises identifying the types of the brackets to a user. Alternatively, the method further includes where identifying the types of the brackets to the user comprises identifying a prescription of each corresponding bracket including but not limited to at least one torque applied to the bracket or at least one tip machined into a bracket slot for each corresponding tooth.

In another embodiment, the method above further includes where employing the plurality of brackets according to the recorded information scanned from the corresponding RFID chip comprises identifying the brackets in an area of the mouth, or identifying the brackets in the entire mouth in order to produce a patient tooth chart of each bracket location, prescription, including wire slot size, a tip defined in the bracket, a torque applied to the bracket, and/or material of manufacture of the bracket.

In yet another embodiment, the method above further comprises replacing a plurality of brackets when a change in prescription is needed comprising scanning the outdated brackets being replaced prior to removal, replacing the current patient information with updated scanned information, and documenting a reason the brackets are being replaced in a patient tooth chart correlated to the scanned identification. Alternatively, the method further comprises scanning a plurality of replacement brackets to insure that the replacement brackets are the desired brackets with a proper corresponding prescription.

In yet another embodiment, the method above further includes where identifying the brackets in an area of the mouth or identifying the brackets in the entire mouth further comprises integrating the identification with a practice management program and attaching it to a patient tooth chart.

The invention also teaches of an apparatus comprising a radio frequency identification (RFID) microchip, an orthodontic bracket the RFID microchip coupled to, in or on the bracket, where the RFID chip has recorded thereon information concerning the nature of the bracket, a scanner for scanning the recorded information from the RFID microchip coupled to the at least one bracket, and means for employing the bracket according to the recorded information scanned from the corresponding RFID microchip.

Finally, the current invention provides for a software product including instructions stored on a tangible medium for controlling a computer comprising, means for scanning recorded information from a plurality RFID chips coupled to a corresponding plurality of brackets, means for interpreting the recorded information from each of the plurality of RFID chips coupled to, on or in a plurality of orthodontic brackets, where the RFID chips have recorded therein information concerning, coded or related to the nature of each corresponding bracket, and based on the interpreted recorded information, means: for determining an inventory of the brackets, for identifying the types of the brackets to a user, for identifying a prescription of each corresponding bracket including but not limited to at least one torque applied to the bracket or at least one tip machined into a bracket slot for each corresponding tooth, for identifying the brackets in an area of the mouth, for identifying the brackets in the entire mouth in order to produce a patient tooth chart of each bracket location, prescription, including wire slot size, a tip defined in the bracket, a torque applied to the bracket, and/or material of manufacture of the bracket, for scanning the outdated brackets being replaced prior to removal, replacing the current patient information with updated scanned information, and documenting a reason the brackets are being replaced in a patient tooth chart correlated to the scanned identification, for scanning a plurality of replacement brackets to insure that the replacement brackets are the desired brackets with a proper corresponding prescription, and/or for integrating the identification with a practice management program and attaching it to a patient tooth chart.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The illustrated embodiments of the invention include an apparatus and method for quickly determining the type of bracket installed or to be installed on patient's tooth. A radio frequency identification (RFID) microchip is coupled to, on or in an orthodontic bracket. The bracket or series of brackets are then installed on the patient's tooth or teeth as required. With the RFID in or on the bracket, the orthodontist or staff uses a scanner to read the brackets, which are installed on the patient's teeth. The information read by the scanner allows the practitioner to select the correct corresponding bracket(s) needed for replacement or additional missing brackets needed to be drawn from an inventory. Confirmation of the correct selection from the inventory is obtained by another scan from another scanner located in the bracket holding device. Not only does this process ensure that the correct replacement bracket is received by the patient, but also provides the orthodontist and staff with a real-time tracking of inventory supply.

Figure 1:
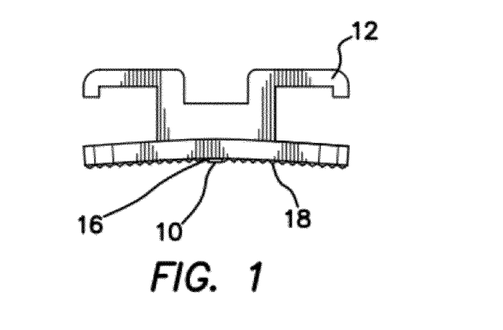
FIG. 1 is side planar view of the RFID bracket with the RFID microchip coupled to the bottom of the bracket.
Figure 2:
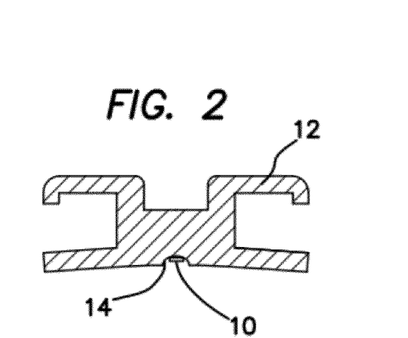
FIG. 2 is side cross-sectional planar view of the RFID bracket with the RFID microchip coupled to the bottom of the bracket.

Attachment of an RFID microchip 10 to a metal, ceramic or hard plastic resin bracket 12 is illustrated in FIGS. 1-4. It is to be expressly understood that the resin bracket 12 may be either the ligated or self-ligated type or any other type of bracket now known or later devised. The RFID microchip 10 may be placed in a depression 14 on the tooth side base of the bracket 12 as shown in FIG. 2, which is a "hole" 16 in a mesh backing 18 of the metal bracket 10 as seen in FIG. 1, or adhered to the lip side 22 of the bracket 10 or in a depression or cup 20 and sealed over with a resin sealant as shown in plan view in FIG. 3 or cross-sectional view in FIG. 4.

Figure 3:
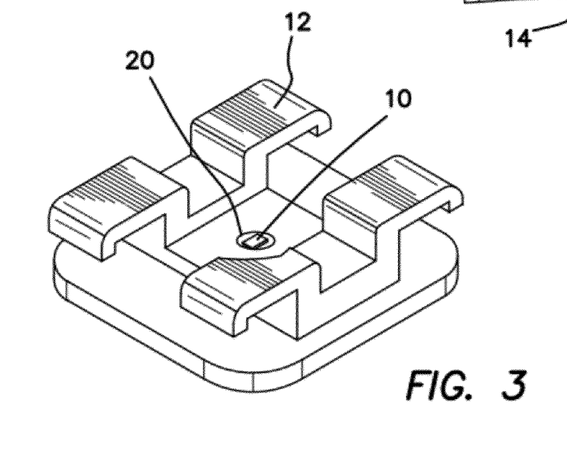
FIG. 3 is a perspective view of the RFID bracket with the RFID microchip coupled to the top of the bracket.
Figure 4:
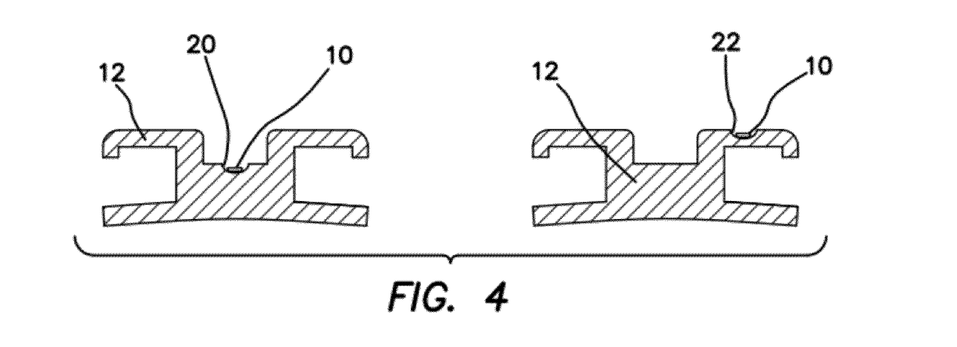
FIG. 4 is a planar cross-section planar view of the RFID bracket with the RFID microchip coupled to the top of the bracket and a planar cross-sectional view of the RFID bracket with the RFID microchip coupled to the lip of the bracket.

The advantage of the lip side shown in FIG. 3 is that the RFID microchip 10 is not shielded by the tooth (not shown) or the bracket 12 and can transmit without interference when activated. Also, placement of the RFID chip would be less likely to have any potential effect on the tooth.

In another embodiment, a plurality of brackets 12 may be coupled to a plurality of teeth, each bracket 12 comprising a corresponding RFID microchip 10 and thus forming a network of brackets.

Each RFID microchip 10 comprises the ability to identify features included but not limited to the tip, torque, and slot dimensions of the bracket and might include additional information such as the manufacturer and material of manufacture. A complete complement of braces could include brackets 12 of different prescriptions being placed on each tooth, the prescriptions varying even for the same tooth with each bracket 12 on each opposing side of the tooth varying from one another. The identity or information related to each bracket 12 is coded into a unique number stored on each corresponding RFID chip 10.

Figure 5:
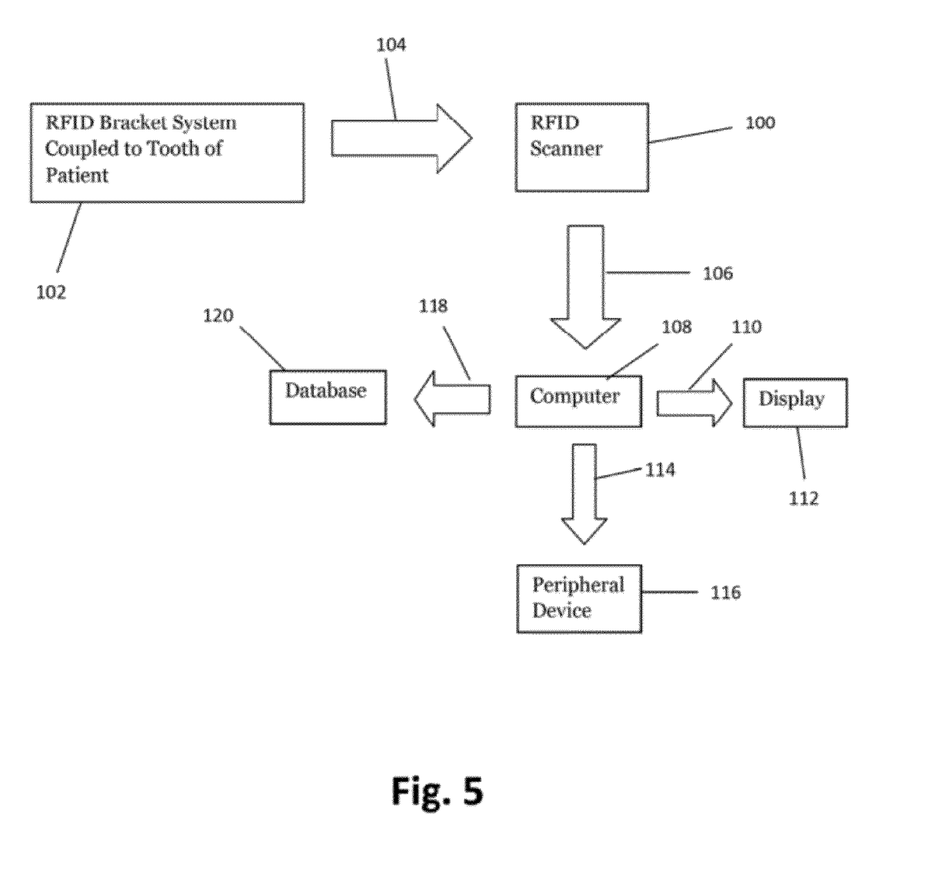
FIG. 5 is a block diagram of the procedure taken by the RFID bracket system when an RFID microchip is being scanned.

In one embodiment shown in the block diagram of FIG. 5, the RFID scanner 100 reads the information imprinted on the RFID bracket system 102 coupled to the tooth or teeth of a patient via step 104. It is to be expressly understood that the RFID scanner 100 may read the identification information off a RFID bracket system 102 that comprises a single bracket and RFID microchip, or off a plurality of RFID microchips and brackets that constitute a portion or the entirety of the patients mouth. The RFID scanner 100 then produces a list or chart of the RFID bracket system 102 in place within patient's mouth complete with each bracket's particular prescription, including wire slot sizes, tips, torques, and material of manufacture and then transmits that list or chart to a computer 108 at step 106. It is to be expressly understood that other features of the orthodontic bracket not listed within the current application now in use or later devised may also be scanned by the current device without departing from the original spirit and scope of the invention.

A user at computer 108 may then take the RFID bracket system 102 information sent by the RFID scanner 100 and store it to an internal database 120 via step 118. Alternatively, the user may also display the acquired information on a display 112 coupled to the computer 108 at step 110, or send the information out to a peripheral device 116 at step 114. The peripheral device 116 may comprise any one or combination of a plurality of devices including printers, copiers, web servers, or other networked computers. Additionally, the peripheral device may include an external memory device such as a FLASH drive or compact disc.

Figure 6:
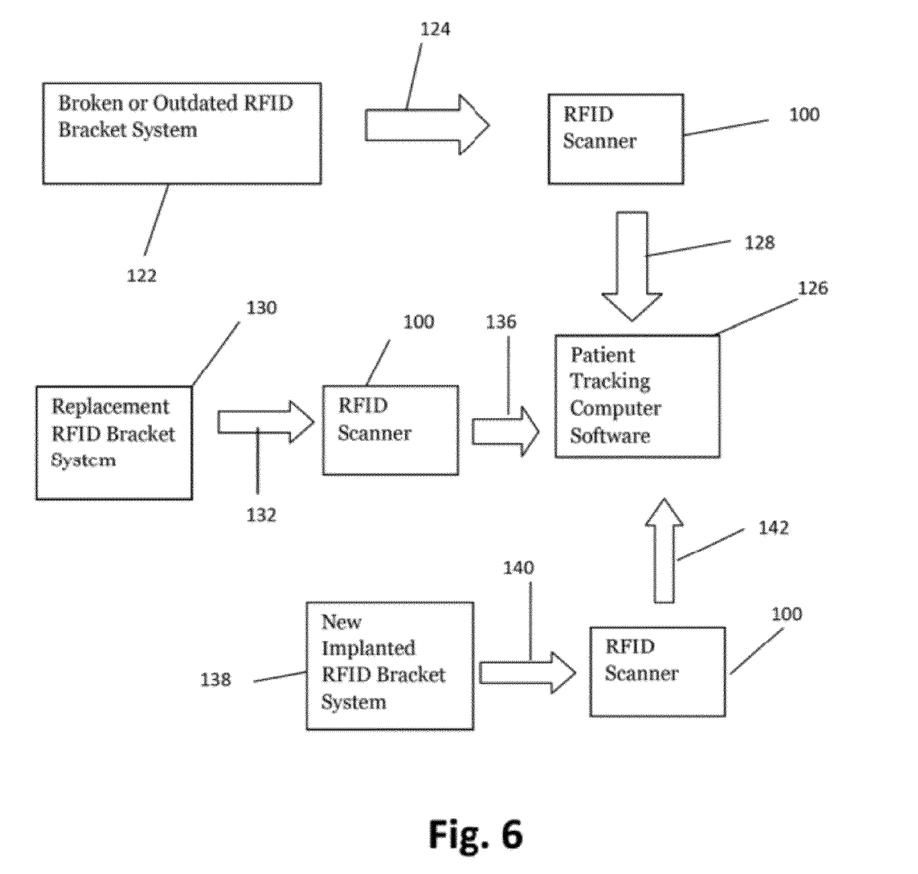
FIG. 6 is a block diagram of the procedure taken by the RFID bracket system when a broken or outdated RFID microchip is being replaced.

If the bracket 12 becomes broken or replacement is required in order to change the prescription, the method of the illustrated embodiment in the block diagram of FIG. 6 scans the broken or outdated RFID bracket system 122 being replaced with the RFID scanner 100 at step 124. The RFID scanner 100 then replaces the outdated patient information with updated information for that patient and adds this data to a patient tracking computer software program 126 at step 128 to document the reason the bracket is being replaced allowing the orthodontist to build a data base of the brackets most commonly replaced for whatever reason, including but not limited to wrong choice of bracket prescription, less than adequate response, bond failure, or need to reposition due to positioning error. This process helps identify issues affecting the efficiency of treatment without having to laboriously enter this data manually and reduce the possibility of incorrect patient treatment.

Prior to replacing the old bracket, a replacement RFID bracket system 130 is scanned by an RFID scanner 100 at step 132 to be sure in fact that the new bracket being implanted is the proper bracket with the proper prescription which can be an issue even with bracket packaging clearly marked. Information scanned off of the new bracket 130 is turn uploaded to the patient tracking computer software 126 via step 136. This feature is also helpful when brackets are to be placed indirectly in a laboratory setting prior to transfer to the patient's mouth. It would not only document for the lab the brackets 12 used, but verify the correctness which, at this time, is a totally blind process for the orthodontist. Currently, the orthodontist must trust the fact that the lab technician placed the intended bracket in the tray for installation.

Once the brackets are placed through direct or indirect placement, the orthodontist scans the entire newly placed RFID bracket system 138 with the RFID scanner 100 at step 140. The information received from the newly placed RFID bracket system 138 is then sent into the patient tracking computer software program 126 at step 142. The patient tracking computer software 126 is integrated with a practice management program (not shown) and is attached to the patient's individual tooth chart within the computer 108. The tooth chart therefore represents the entirety of the patient's treatment from start to finish and shows what RFID bracket system was scanned at each step along the way which assures a high degree of accuracy and efficiency. The scanned data is then resident in the patient's electronic chart and available for quick access.

Figure 7:
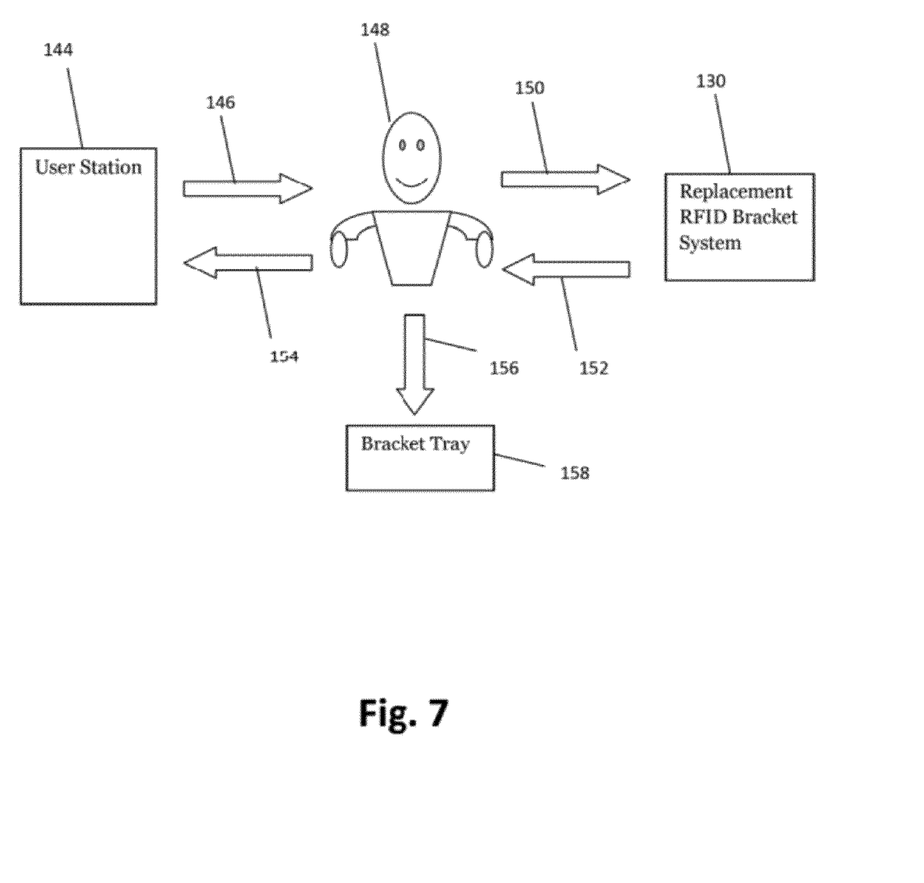
FIG. 7 is a block diagram of the procedure taken by the RFID bracket system when used in a robotic system of bracket placement.

In another embodiment depicted in FIG. 7, the RFID chip and scanner is used in a robotic system of bracket placement for preparation of indirect or direct bonding trays or devices. A user at a user station 144 enters the corresponding information for a particular RFID bracket system 130 for which he is searching into the user station 144, which for example may be a networked computer or a software program module within a computer. The user station 144 sends the entered data to a robot 148 at step 146. The robot 148 moves to where the replacement RFID bracket system 130 is located at step 150 and reads the information of the RFID chip 10 at step 152. The robot 148 and then verifies and documents the choice with the user station 144 at step 154. Alternatively, step 152 comprises the step of the robot 148 physically removing the replacement RFID bracket system 130 from its location. The robot 148 then deposits the replacement RFID bracket system 130 in a bracket tray 158 or other predetermined physical location at step 156.

Figure 8:
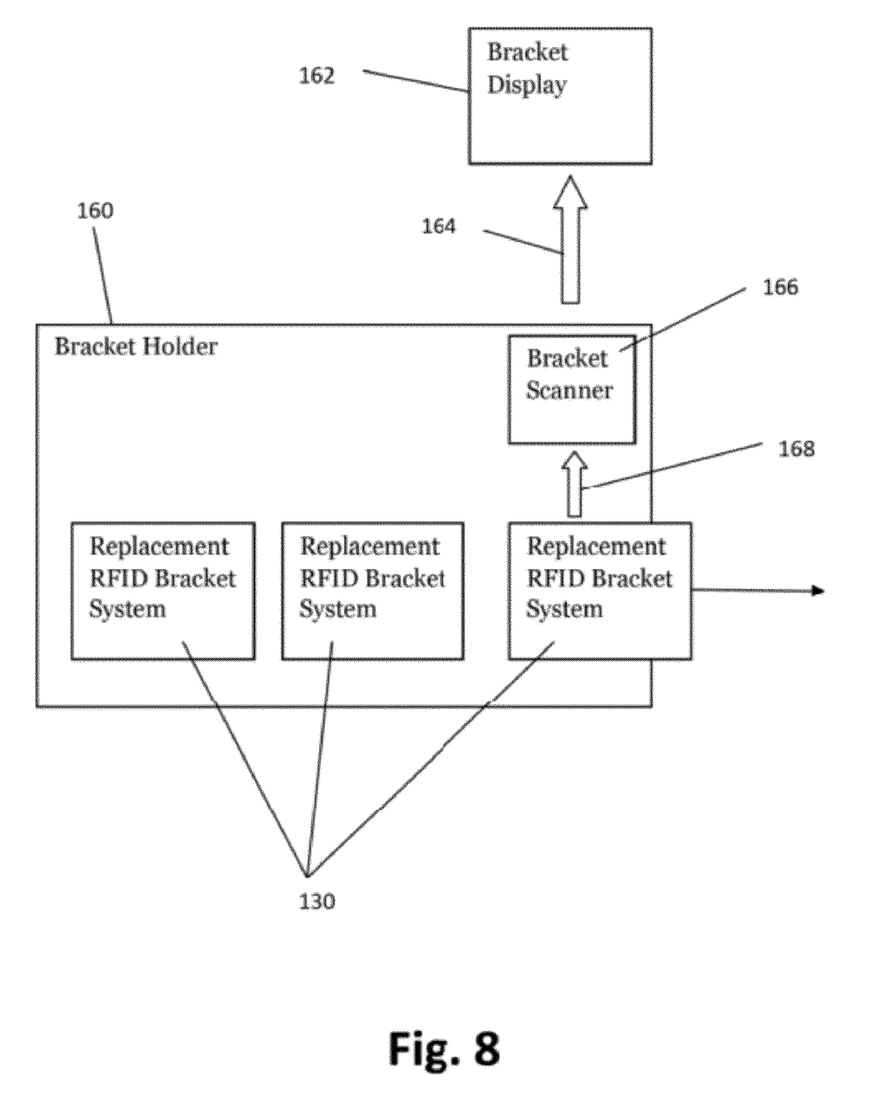
FIG. 8 is a block diagram of the procedure taken by the RFID bracket system when used in conjunction with a bracket holder.

In another embodiment depicted in FIG. 8, the RFID chip and scanner is built into a bracket holding device 160, which is capable of holding a plurality of replacement RFID bracket systems 130. As a replacement RFID bracket system 130 is being removed from the bracket holder 160, it passes underneath a bracket scanner 166 which scans the information from the RFID bracket system at step 168. As soon as the RFID bracket system 130 is picked up by the bracket scanner 166, the scanned information is sent to a bracket display screen 162 coupled to the bracket holder 160 via step 164. The bracket display screen 162 displays the relevant prescription information to the user, again preventing the selection and subsequent placement of incorrect brackets.

In another embodiment, the RFID chip 10 also functions during x-ray and optical dental scans to give the correct information to the relevant software programs which then use the scanned x-ray and optical dental scans to bend custom wires or plan treatment with specialized dental programs.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

For example, the RFID microchip 10 may be coupled to one or multiple locations on the bracket 12 other than those specified above and shown in the figures.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method of using radio frequency identification (RFID) microchips in an orthodontic bracket comprising:
    providing at least one orthodontic bracket with at least one RFID chip coupled to, in or on the at least one orthodontic bracket, where the at least one RFID chip has recorded thereon bracket information concerning a set of features of the at least one orthodontic bracket;
    scanning the recorded bracket information from the at least one RFID chip coupled to the at least one orthodontic bracket; and
    employing the at least one orthodontic bracket according to the recorded information scanned from the corresponding at least one RFID chip,
    wherein employing the at least one orthodontic bracket according to the recorded information scanned from the corresponding at least one RFID chip comprises using the at least one RFID chip during x-ray and optical dental scans to give scanned information to a software program which uses the scanned recorded information to bend custom wires or plan treatment with specialized orthodontic programs.

2. The method of claim 1 wherein employing the at least one orthodontic bracket according to the recorded information scanned out of the corresponding at least one RFID chip comprises using the recorded bracket information for determining an inventory of the at least one bracket.

3. The method of claim 1 wherein employing the at least one orthodontic bracket according to the recorded information read out of the corresponding at least one RFID chip comprises identifying a type of the at least one orthodontic bracket to a user.

4. The method of claim 3 where the at least one orthodontic bracket includes at least one tip machined into a bracket slot and where identifying the type of at least one orthodontic bracket to the user comprises identifying a prescription of the corresponding at least one bracket including but not limited to at least one torque applied to the at least one orthodontic bracket and/or tip machined into the bracket slot for each corresponding tooth.

5. The method of claim 1 where employing the at least one orthodontic bracket according to the recorded information scanned out of the corresponding at least one RFID chip comprises identifying a particular targeted bracket in order to produce a patient tooth chart of a location, prescription, including wire slot size, tip structure, torque applied to the bracket, and/or material of manufacture of the at least one orthodontic bracket.

6. The method of claim 1 further comprising replacing the at least one orthodontic bracket when a change in prescription is needed comprising:
scanning the at least one orthodontic bracket being replaced prior to removal;
replacing a current set of patient information with an updated set of scanned information; and
documenting in a patient tooth chart correlated to the updated set of scanned information a reason the at least one orthodontic bracket is being replaced.

7. The method of claim 6 further comprising scanning a replacement bracket to insure that the replacement bracket has a proper prescription.

8. The method of claim 1 where the steps of scanning the recorded bracket information from the at least one RFID chip coupled to the at least one bracket and employing the at least one bracket according to the recorded bracket information scanned out of the corresponding at least one RFID chip further comprises:
sending a set of user-entered conditions to a robotic system;
the robotic system selecting a bracket based on the set of user-entered conditions;
the robotic system scanning the selected bracket;
the robotic system confirming that the selected bracket has the set of user-entered conditions; and
the robotic system recording that the selected bracket has been confirmed with having the set of user-entered conditions.

9. The method of claim 8 further comprising the robotic system performing bracket placement into an indirect or direct bonding tray.

10. The method of claim 1 where scanning the recorded bracket information from the at least one RFID chip coupled to the at least one bracket comprises:
scanning the at least one bracket with an RFID scanner disposed within a bracket holding device to scan the recorded bracket information from the at least one RFID chip while the bracket is being held within the at least one bracket holding device; and
displaying the recorded bracket information on a display coupled to the bracket holding device.

11. A method of using radio frequency identification (RFID) microchips in an orthodontic bracket comprising:
providing a plurality of RFID chips coupled to, on or in a plurality of orthodontic brackets, where the plurality of RFID chips have recorded therein information concerning a set of features of the corresponding plurality of orthodontic brackets;
scanning the recorded information from the plurality of RFID chips coupled to the plurality of orthodontic brackets; and
employing the plurality of orthodontic brackets according to the recorded information scanned out of the corresponding plurality of RFID chips,
wherein employing the plurality of orthodontic brackets according to the recorded information scanned from the corresponding plurality of RFID chips comprises using the plurality of RFID chips during x-ray and optical dental scans to give scanned information to a software program which uses the scanned recorded information to bend custom wires or plan treatment with specialized orthodontic programs.

12. The method of claim 11 wherein employing the plurality of orthodontic brackets according to the recorded information scanned from the corresponding plurality of RFID chips comprises using the information for determining an inventory of the plurality of orthodontic brackets.

13. The method of claim 11 wherein employing the plurality of orthodontic brackets according to the recorded information scanned from the corresponding plurality of RFID chips comprises identifying a type for each of the plurality of orthodontic brackets to a user.

14. The method of claim 13 where identifying the types for each of the plurality of orthodontic brackets to the user comprises identifying a prescription of the corresponding plurality of orthodontic brackets including but not limited to at least one torque applied to the plurality of orthodontic brackets or at least one tip machined into a bracket slot for each corresponding tooth.

15. The method of claim 11 where employing the plurality of orthodontic brackets according to the recorded information scanned from the corresponding plurality of RFID chip comprises:
identifying the plurality of orthodontic brackets in an area of the mouth; or
identifying the plurality of orthodontic brackets in the entire mouth in order to produce a patient tooth chart of a location, prescription, including wire slot size, tip structure, torque applied to the bracket, and/or material of manufacture of each of the plurality of orthodontic brackets.

16. The method of claim 11 further comprising replacing a plurality of orthodontic brackets when a change in prescription is needed comprising:
scanning the plurality of orthodontic brackets being replaced prior to removal;
replacing a set of current patient information with an updated set of scanned information; and
documenting a reason the plurality of orthodontic brackets are being replaced in a patient tooth chart correlated to the scanned recorded identification.

17. The method of claim 16 further comprising scanning a plurality of replacement brackets to insure that the plurality of replacement brackets have a proper corresponding prescription.

18. The method of claim 15 where identifying the plurality of orthodontic brackets in an area of the mouth or identifying the plurality of orthodontic brackets in the entire mouth further comprises integrating the identification of the plurality of orthodontic brackets with a practice management program and attaching the practice management program to a patient tooth chart.

19. An apparatus comprising:

a radio frequency identification (RFID) microchip;

an orthodontic bracket; the RFID microchip coupled to, in or on the said orthodontic bracket, where the RFID microchip has recorded thereon information concerning a set of features of the orthodontic bracket;

a scanner for scanning the recorded information from the RFID microchip coupled to the orthodontic bracket; and means for employing the orthodontic bracket according to the recorded information scanned from the corresponding RFID microchip, wherein the means for employing the orthodontic bracket according to the recorded information scanned from the corresponding RFID chip comprises using the RFID microchip during x-ray and optical dental scans to give scanned information to a software program which uses the scanned recorded information to bend custom wires or plan treatment with specialized orthodontic programs.

* * * * *